(12) United States Patent
Tsuang et al.

(10) Patent No.: US 12,396,759 B2
(45) Date of Patent: Aug. 26, 2025

(54) MINIMALLY INVASIVE AND ENDOSCOPIC SPINAL FIXATION DEVICE

(71) Applicant: CHANPIN MEDTAK CO., LTD., New Taipei (TW)

(72) Inventors: Fon-Yih Tsuang, New Taipei (TW); Chang-Jung Chiang, New Taipei (TW); Yueh-Ying Hsieh, New Taipei (TW); Ting-Shuo Hsu, New Taipei (TW); Po-Yi Liu, New Taipei (TW)

(73) Assignee: CHANPIN MEDTAK CO., LTD., New Taipei (TW)

( * ) Notice: Subject to any disclaimer, the term of this patent is extended or adjusted under 35 U.S.C. 154(b) by 160 days.

(21) Appl. No.: 18/276,536

(22) PCT Filed: Feb. 9, 2022

(86) PCT No.: PCT/US2022/015771
§ 371 (c)(1),
(2) Date: Aug. 9, 2023

(87) PCT Pub. No.: WO2022/173797
PCT Pub. Date: Aug. 18, 2022

(65) Prior Publication Data
US 2024/0000484 A1    Jan. 4, 2024

Related U.S. Application Data

(60) Provisional application No. 63/147,278, filed on Feb. 9, 2021.

(51) Int. Cl.
*A61B 17/86* (2006.01)
*A61B 17/70* (2006.01)
*A61B 17/00* (2006.01)

(52) U.S. Cl.
CPC ...... *A61B 17/7001* (2013.01); *A61B 17/8605* (2013.01); *A61B 17/863* (2013.01); *A61B 17/8685* (2013.01); *A61B 2017/00238* (2013.01)

(58) Field of Classification Search
CPC .................. A61B 17/8685; A61B 17/7001
See application file for complete search history.

(56) References Cited

U.S. PATENT DOCUMENTS

| | | | |
|---|---|---|---|
| 2007/0213732 A1* | 9/2007 | Khanna | A61B 17/8685 606/86 A |
| 2008/0086131 A1 | 4/2008 | Daly | |
| 2009/0093843 A1 | 4/2009 | Lemoine | |
| 2011/0190821 A1 | 8/2011 | Chin | |
| 2013/0072981 A1 | 3/2013 | Jackson | |
| 2016/0206358 A1 | 7/2016 | Zhao | |
| 2018/0028245 A1* | 2/2018 | Ziemek | A61B 17/8695 |
| 2019/0038427 A1 | 2/2019 | Fleischer | |
| 2019/0254724 A1 | 8/2019 | McClintock | |
| 2020/0163701 A1 | 5/2020 | Ballard | |

* cited by examiner

*Primary Examiner* — Olivia C Chang
(74) *Attorney, Agent, or Firm* — WPAT, PC

(57) ABSTRACT

The present disclosure provides a spinal fixation device, including a spinal fixation pedicle screw and an outer oval sheath. The spinal fixation device is provided with at least one locking structure and the outer oval sheath is locked to the spinal fixation pedicle screw through the at least one locking structure. The spinal fixation device can strengthen the stability of the spinal fixation pedicle screw for fixation after implantation in vertebrae during the spinal surgery.

17 Claims, 7 Drawing Sheets

MINIMALLY INVASIVE AND ENDOSCOPIC SPINAL FIXATION DEVICE

CROSS-REFERENCE TO RELATED APPLICATION

This application claims priority of Provisional Application No. 63/147,278, filed on Feb. 9, 2021, and Taiwan patent application No. 111103978, filed on Jan. 28, 2022, the content of which is incorporated herein in its entirety by reference.

BACKGROUND OF THE INVENTION

1. Field of the Invention

The present invention relates to a spinal fixation device.

2. The Prior Art

The spine is one of the most important parts in determining human mobility. When the spine is diseased, especially in the lumbar region, it often has a considerable impact on patients, including pain and numbness, weakness, or even symptoms such as incontinence or difficulty urinating. The above symptoms are caused by the translocation between the vertebral bodies and the compression of the nerve or spinal cord, and the clinical diagnosis can be divided into intervertebral disc herniation, spondylolisthesis, spinal stenosis or degenerative idiopathic scoliosis due to different causes. When the symptoms are severe, patients often cannot improve their discomfort through correction, and must rely on spinal surgery for reduction treatment. As for how to effectively fix the vertebral body after reduction to avoid re-displacement, it is an important key to the success of the treatment.

At present, the most stable and widely used treatment method is the use of a pedicle screw fixation system. The pedicle screw fixation system can be used in spinal fusion surgery such as vertebral segment fixation and reduction after traditional discectomy, cervical spine degeneration treatment and scoliosis correction.

The pedicle screw body is mainly a cylindrical structure with a circular cross section and is designed with a thread. The implantation site of the pedicle screw is at the back of the spine. The implantation site is generally selected at the junction of the lateral side of the superior articular process and the transverse process of the vertebral arch, and then the pedicle screw passes through the pedicle and enters the anterior vertebral body.

From the perspective of the anatomical structure of the vertebral body, the vertebral arch has an elliptical cross-sectional structure, and it is also the only part in contact with the cortical bone after the pedicle screw is locked. Compared with the anterior column of the vertebral body, the vertebral arch is the main force bearing site. The stability of the pedicle region after pedicle screw implantation is an important factor that mainly affects whether the pedicle screw is loosened or not.

The pedicle screw fixation system uses the movable unit that fixes a vertebra as a minimum fixed unit, so four pedicle screws and two metal rods are required. This fixation system provides immediate stabilization of the spine after surgery, increasing the chance of interbody fusion and healing of vertebral fractures.

However, although the pedicle screw with circular section can provide a good initial stabilization effect after being implanted into the spine, the failure of the pedicle screw fixation still often occurs. If the fixation effect is found to be poor during or after the operation, resulting in the loosening of the spinal screws, resulting in the failure of the entire posterior fixator of the spine, the failure of the operation would cause the patient to have pain recurrence or require a second operation, causing greater distress to the patient. In-depth discussion of the reasons for the failure of the pedicle screw is needed. During the movement of the vertebral body, the spine is subjected to coupling forces, such as bending moment, tension, pressure and torsion. Excessive coupling forces would cause the interface between the screw body and the vertebral body to generate more stress than the bone can bear, resulting in the loss of bone around the pedicle screw with the circular section, resulting in a gap between the screw body and the vertebral body connection interface and loosening.

In order to solve the above-mentioned problems, those skilled in the art need to develop a novel spinal fixation device for the benefit of a large group of people in need thereof. The present invention starts from the design of the pedicle screw body, and changes the geometric configuration of the pedicle screw fixation system at the vertebral arch to increase the contact surface area between the pedicle screw body and the vertebral arch. While reducing the stress of the vertebral arch, it also increases the structural strength of the pedicle screw and reduces the risk of bone loss.

SUMMARY OF THE INVENTION

A primary objective of the present invention is to provide a spinal fixation device, comprising a spinal fixation pedicle screw and an outer oval sheath. The spinal fixation pedicle screw includes a cup head and a screw body connected with the cup head, wherein a longitudinal perforation is formed from a top of the cup head to a bottom of the screw body, and the screw body is provided with at least one locking structure. The outer oval sheath has a shape of a hollow column, wherein the outer oval sheath is locked to the screw body of the spinal fixation pedicle screw through the at least one locking structure.

According to an embodiment of the present invention, the outer oval sheath has a transverse section in an oval outer diameter.

According to an embodiment of the present invention, the at least one locking structure includes a first thread close to the cup head and a second thread adjacent to the first thread and close to the bottom.

According to an embodiment of the present invention, the outer oval sheath passes through the second thread and is locked to the first thread, and the outer oval sheath covers the first thread.

According to an embodiment of the present invention, a thread pitch of the first thread is not equal to that of the second thread.

According to an embodiment of the present invention, a thread pitch of the first thread is less than that of the second thread.

According to an embodiment of the present invention, the outer oval sheath includes an outer wall surface and an inner wall surface opposite to the outer wall surface, and the inner wall surface is in contact with the first thread.

According to an embodiment of the present invention, the inner wall surface is provided with a third thread, and the third thread cooperates with the first thread to lock the outer oval sheath to the first thread.

According to an embodiment of the present invention, the outer wall surface is a smooth surface.

According to an embodiment of the present invention, the outer wall surface is provided with a fourth thread.

According to an embodiment of the present invention, the outer oval sheath has a long axis of 4 mm to 19 mm and a short axis of 3 mm to 17 mm, and a ratio of the long axis to the short axis is greater than or equal to 1.0.

According to an embodiment of the present invention, the outer oval sheath has a height of 3 mm to 20 mm.

According to an embodiment of the present invention, the spinal fixation pedicle screw has a diameter of 3 mm to 11 mm.

According to an embodiment of the present invention, a distance between the inner wall surface and the outer wall surface is 1 mm.

According to an embodiment of the present invention, the outer oval sheath is made of metal or plastic.

According to an embodiment of the present invention, the metal is titanium alloy or stainless steel.

According to an embodiment of the present invention, the plastic is polylactic acid (PLA), poly(lactic-co-glycolic acid) (PLGA), polycarbonate (PC) or poly(ether-ether-ketone) (PEEK).

In summary, the spinal fixation device of the present invention has the following effect. The spinal fixation device is provided with at least one locking structure and the outer oval sheath is locked to the spinal fixation pedicle screw through the at least one locking structure. The spinal fixation device can strengthen the stability of the spinal fixation pedicle screw for fixation after implantation in vertebrae during the spinal surgery.

The maximum stress at the vertebral arch after the spinal fixation device is implanted into the vertebral body can be reduced by 10% compared to the pedicle screw fixation system with a circular section.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
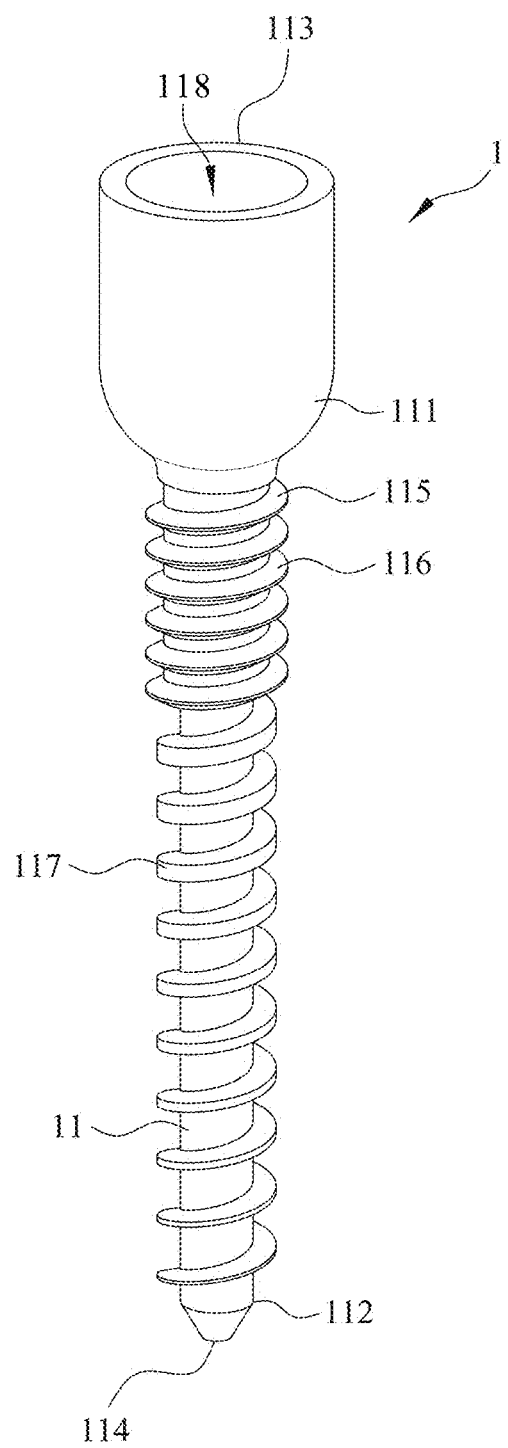
FIG. 1 is a schematic diagram of an embodiment of a spinal fixation pedicle screw of a spinal fixation device.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

DEFINITION

As used herein, the numerical values are approximations and all experimental and dimensional data are expressed within 20%.

Embodiments of the spinal fixation device according to the present invention would be described below with reference to the related drawings, wherein the same elements would be described with the same reference numerals.

The spinal fixation device is provided with at least one locking structure and the outer oval sheath is locked to the spinal fixation pedicle screw through the at least one locking structure. The spinal fixation device can strengthen the stability of the spinal fixation pedicle screw for fixation after implantation in vertebrae during the spinal surgery. The structures and features of the spinal fixation device of the present invention would be described with the following examples.

Referring to FIG. 1 to FIG. 4, which are schematic diagrams of an embodiment of a spinal fixation device 1. The spinal fixation device 1 comprises a spinal fixation pedicle screw 11 and an outer oval sheath 12. The spinal fixation pedicle screw 11 includes a cup head 111 and a screw body 112 connected with the cup head 111, wherein a longitudinal perforation 118 is formed from a top 113 of the cup head 111 to a bottom 114 of the screw body 112, and the screw body 112 is provided with at least one locking structure 115. The outer oval sheath 12 has a shape of a hollow column, wherein the outer oval sheath 12 is locked to the screw body 112 of the spinal fixation pedicle screw 11 through the at least one locking structure 115.

In the present embodiment, the outer oval sheath 12 has a transverse section in an oval outer diameter. The outer oval sheath 12 has at least three different embodiments, see FIGS. 2A to 2C.

In the present embodiment, the number of the at least one locking structure 115 is two, including a first thread 116 close to the cup head 111 and a second thread 117 adjacent to the first thread 116 and close to the bottom 114, see FIG. 1.

Figure 3:
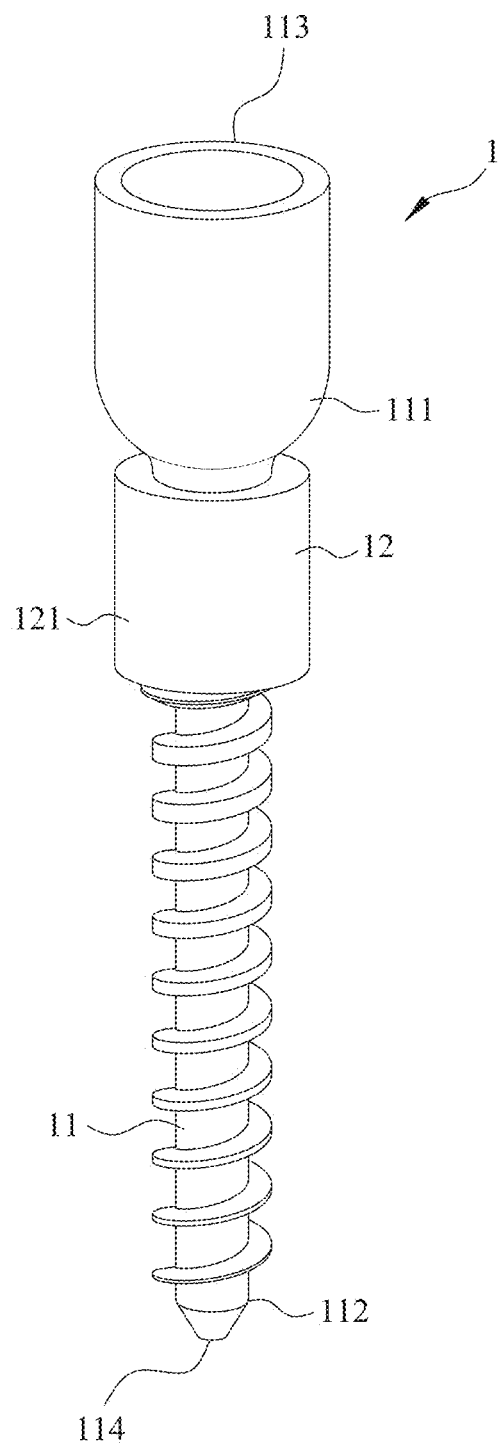
FIG. 3 is a schematic diagram of an embodiment of a spinal fixation pedicle screw and an outer oval sheath of the spinal fixation device.
Figure 4:
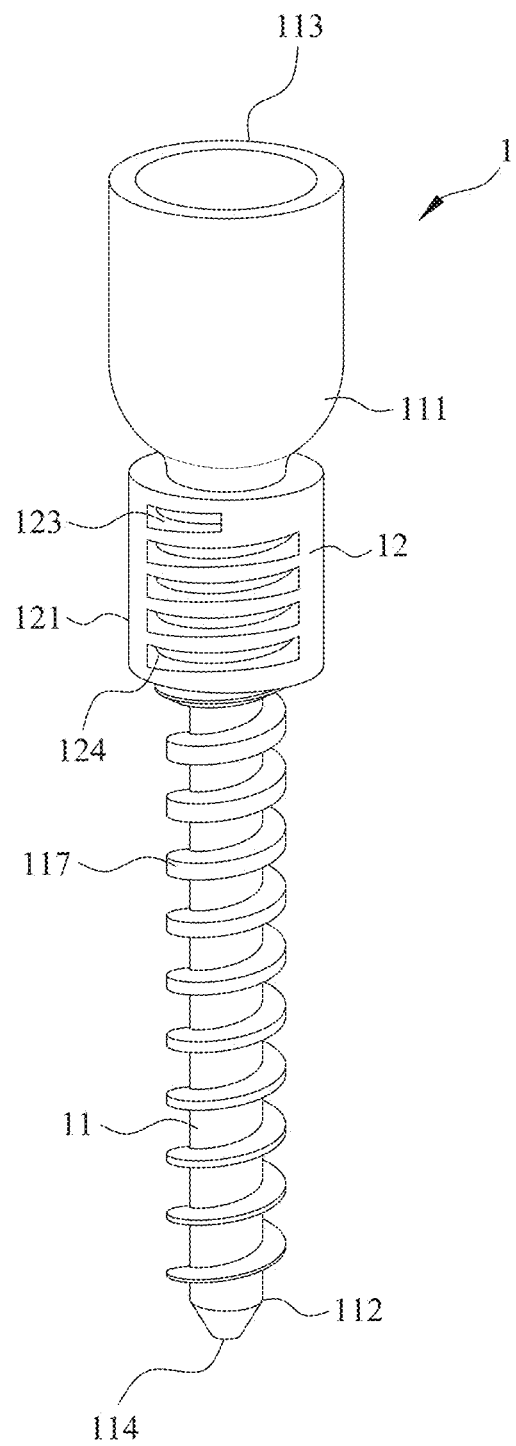
FIG. 4 is a schematic diagram of another embodiment of a spinal fixation pedicle screw and an outer oval sheath of the spinal fixation device.

In the present embodiment, the outer oval sheath 12 passes through the second thread 117 and is locked to the first thread 116, and the outer oval sheath 12 covers the first thread 116, see FIG. 3 and FIG. 4.

In the present embodiment, a thread pitch of the first thread 116 is not equal to that of the second thread 117. Preferably, a thread pitch of the first thread 116 is less than that of the second thread 117, see FIG. 1.

In the present embodiment, the outer oval sheath 12 includes an outer wall surface 121 and an inner wall surface 122 opposite to the outer wall surface 121, and the inner wall surface 122 is in contact with the first thread 116, see FIG. 2A to FIG. 4.

In the present embodiment, the inner wall surface 122 is provided with a third thread 123, and the third thread 123 cooperates with the first thread 116 to lock the outer oval sheath 12 to the first thread 116, see FIG. 2A to FIG. 4.

Figure 2A:
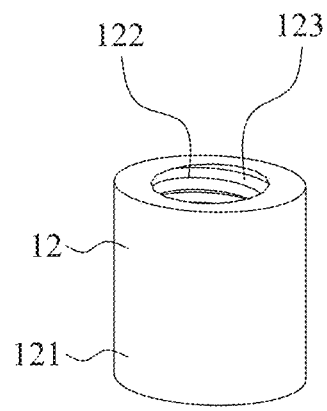
FIGS. 2A to 2C are schematic diagrams of embodiments of an outer oval sheath of a spinal fixation device.

In the present embodiment, the outer wall surface 121 is a smooth surface, see FIG. 2A and FIG. 3.

Figure 2B:
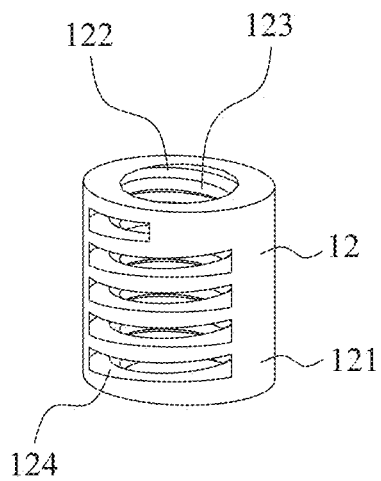

In another embodiment, the outer wall surface 121 is provided with a fourth thread 124, see FIG. 2B and FIG. 4.

In the present embodiment, the outer oval sheath 12 has a long axis of 4 mm to 19 mm and a short axis of 3 mm to 17 mm, and a ratio of the long axis to the short axis is greater than or equal to 1.0.

In the present embodiment, the outer oval sheath 12 has a height of 3 mm to 20 mm.

In the present embodiment, the spinal fixation pedicle screw 11 has a diameter of 3 mm to 11 mm.

In the present embodiment, a distance between the inner wall surface 122 and the outer wall surface 121 is 1 mm. In other words, the oval long diameter of the outer oval sheath 12 is 1 mm from eccentric above and below the center of the screw body 112 of the spinal fixation pedicle screw 11, that is, the diameter of the screw body 112 plus 2 mm is the long diameter of the outer oval sheath 12. In addition, the oval short diameter of the outer oval sheath 12 is the diameter of the screw body 112 of the spinal fixation pedicle screw 11.

In the present embodiment, the outer oval sheath 12 can be made of metal or plastic.

In the present embodiment, the metal is titanium alloy or stainless steel.

In the present embodiment, the plastic is polylactic acid (PLA), poly(lactic-co-glycolic acid) (PLGA), polycarbonate (PC) or poly(ether-ether-ketone) (PEEK).

Figure 2C:
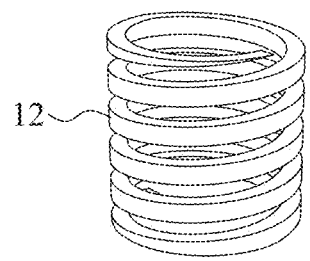

In another embodiment, the outer oval sheath 12 can be in the shape of an oval spring, see FIG. 2C, or an oval tube.

Figure 5:
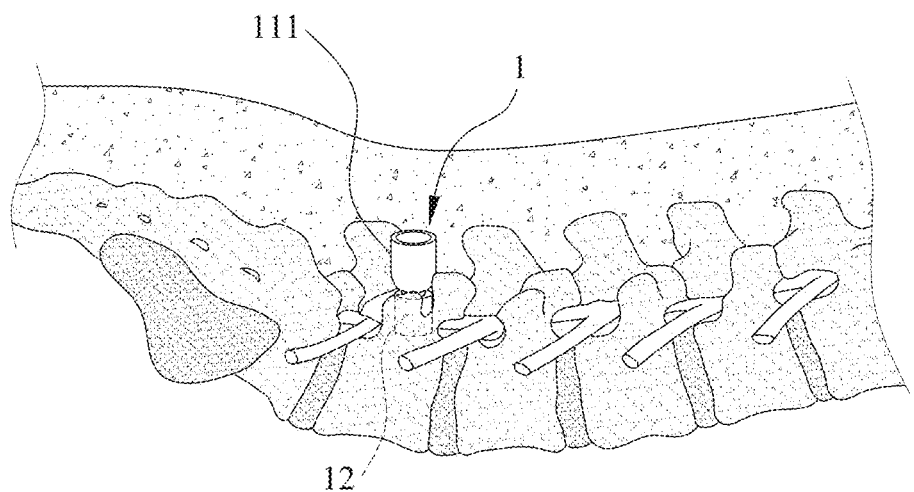
FIG. 5 is a schematic diagram of the operation of the spinal fixation device.

In practice, the spinal fixation device 1 can be positioned by implanting into the vertebrae of a patient who needs to perform spine surgery, and the cup head 111 would be exposed, see FIG. 5.

Figure 6A:
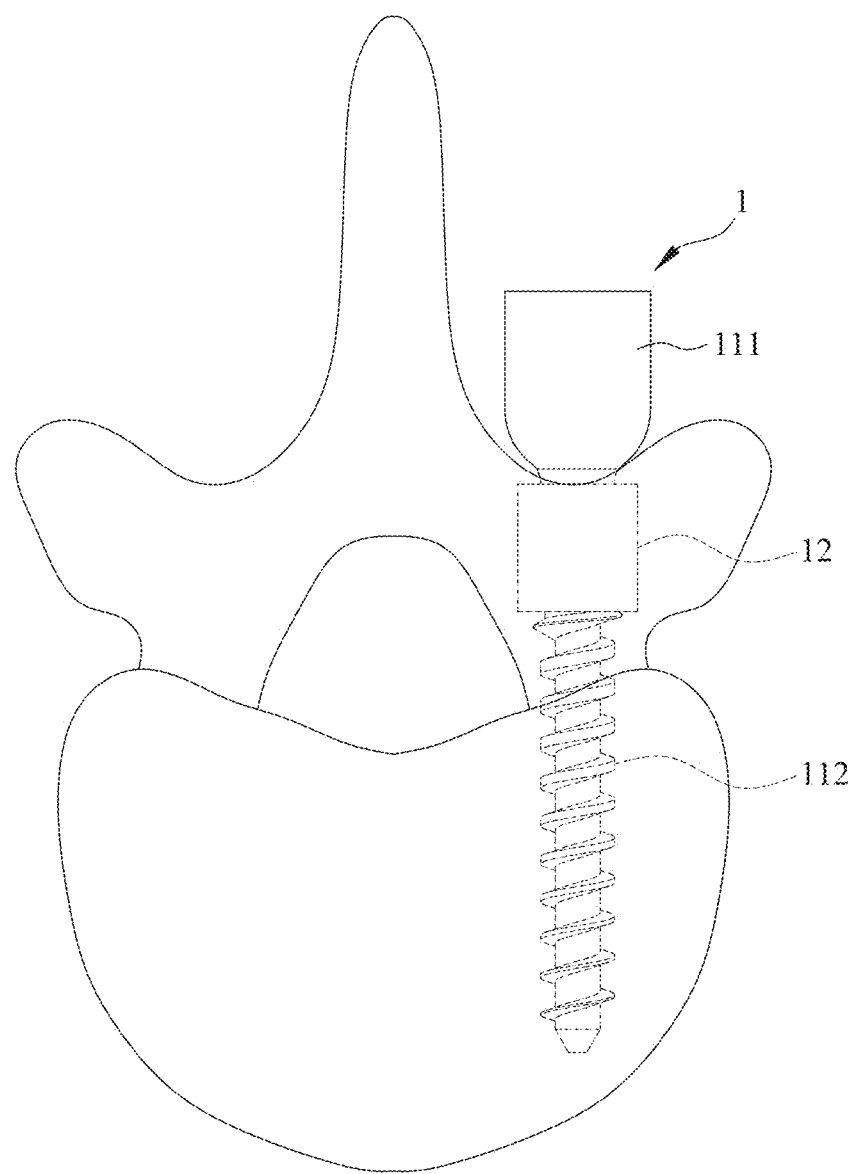
FIGS. 6A and 6B are schematic diagrams of an embodiment of a spinal fixation pedicle screw and an outer oval sheath of the spinal fixation device.
Figure 6B:
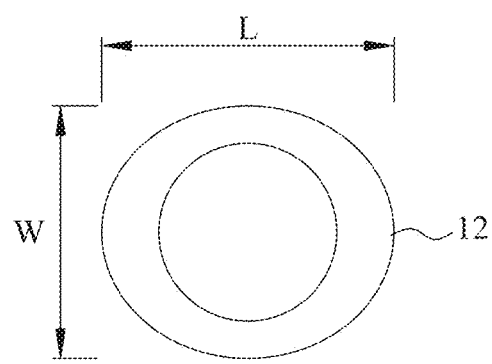

In one embodiment, when the spinal fixation device 1 is implanted into the vertebra, the outer oval sheath 12 is simultaneously embedded in the vertebra, see FIG. 6A. Thereby, the outer oval sheath 12 has a length L (i.e., the long axis) and a width W (i.e., the short axis), wherein the ratio between the length L and the width W is greater than or equal to 1.0 (≥1.0) (see FIG. 6B), and the outer oval sheath 12 with this ratio can provide the best press-fit state, and the fixation and stability of the spinal fixation device 1 can be improved.

In summary, The spinal fixation device 1 is provided with at least one locking structure 115 and the outer oval sheath 12 is locked to the spinal fixation pedicle screw 11 through the at least one locking structure 115. The spinal fixation device 1 can strengthen the stability of the spinal fixation pedicle screw 11 for fixation after implantation in vertebrae during the spinal surgery.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A spinal fixation device, comprising:
    a spinal fixation pedicle screw, including a cup head and a screw body connected with the cup head, wherein a longitudinal perforation is formed from a top of the cup head to a bottom of the screw body, and the screw body is provided with at least one locking structure; and
    an outer oval sheath, having a shape of a hollow column, wherein the outer oval sheath is locked to the screw body of the spinal fixation pedicle screw through the at least one locking structure.

2. The spinal fixation device according to claim 1, wherein the outer oval sheath has a transverse section in an oval outer diameter.

3. The spinal fixation device according to claim 1, wherein the at least one locking structure includes a first thread close to the cup head and a second thread adjacent to the first thread and close to the bottom.

4. The spinal fixation device according to claim 3, wherein the outer oval sheath passes through the second thread and is locked to the first thread, and the outer oval sheath covers the first thread.

5. The spinal fixation device according to claim 3, wherein a thread pitch of the first thread is not equal to that of the second thread.

6. The spinal fixation device according to claim 3, wherein a thread pitch of the first thread is less than that of the second thread.

7. The spinal fixation device according to claim 3, wherein the outer oval sheath includes an outer wall surface and an inner wall surface opposite to the outer wall surface, and the inner wall surface is in contact with the first thread.

8. The spinal fixation device according to claim 7, wherein the inner wall surface is provided with a third thread, and the third thread cooperates with the first thread to lock the outer oval sheath to the first thread.

9. The spinal fixation device according to claim 7, wherein the outer wall surface is a smooth surface.

10. The spinal fixation device according to claim 7, wherein the outer wall surface is provided with a fourth thread.

11. The spinal fixation device according to claim 2, wherein the outer oval sheath has a long axis of 4 mm to 19 mm and a short axis of 3 mm to 17 mm, and a ratio of the long axis to the short axis is greater than or equal to 1.0.

12. The spinal fixation device according to claim 11, wherein the outer oval sheath has a height of 3 mm to 20 mm.

13. The spinal fixation device according to claim 12, wherein the spinal fixation pedicle screw has a diameter of 3 mm to 11 mm.

14. The spinal fixation device according to claim 7, wherein a distance between the inner wall surface and the outer wall surface is 1 mm.

15. The spinal fixation device according to claim 1, wherein the outer oval sheath is made of metal or plastic.

16. The spinal fixation device according to claim 15, wherein the metal is titanium alloy or stainless steel.

17. The spinal fixation device according to claim 15, wherein the plastic is polylactic acid (PLA), poly (lactic-co-glycolic acid) (PLGA), polycarbonate (PC) or poly (ether-ether-ketone) (PEEK).

* * * * *